(12) United States Patent
Brisken et al.

(10) Patent No.: US 6,464,660 B2
(45) Date of Patent: Oct. 15, 2002

(54) BALLOON CATHETERS HAVING ULTRASONICALLY DRIVEN INTERFACE SURFACES AND METHODS FOR THEIR USE

(75) Inventors: Axel Brisken, Fremont; Vartan Ghazarossian, Menlo Park, both of CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 0 days.

(21) Appl. No.: 09/808,725

(22) Filed: Mar. 14, 2001

(65) Prior Publication Data

US 2001/0051784 A1 Dec. 13, 2001

Related U.S. Application Data

(63) Continuation of application No. 09/205,061, filed on Dec. 4, 1998, now Pat. No. 6,287,272, which is a continuation-in-part of application No. 08/708,589, filed on Sep. 5, 1996, now Pat. No. 5,846,218.

(51) Int. Cl.$^7$ ............................................... A61B 17/20
(52) U.S. Cl. ...................... 604/22; 606/108; 604/96.01
(58) Field of Search ............................... 604/22, 96.01; 606/108, 191, 195, 192, 194

(56) References Cited

U.S. PATENT DOCUMENTS

| | | |
|---|---|---|
| 3,433,226 A | 3/1969 | Boyd |
| 3,565,062 A | 2/1971 | Kuris |
| 4,692,139 A | 9/1987 | Stiles |
| 4,698,058 A | 10/1987 | Greenfield et al. |
| 4,808,153 A | 2/1989 | Parisi |
| 4,870,953 A | 10/1989 | DonMichael et al. |
| 4,936,281 A | 6/1990 | Stasz |
| 4,948,587 A | 8/1990 | Kost et al. |
| 5,053,044 A | 10/1991 | Mueller et al. |
| 5,085,662 A | 2/1992 | Willard |
| 5,092,841 A * | 3/1992 | Spears |
| 5,117,831 A | 6/1992 | Jang et al. |
| 5,163,421 A | 11/1992 | Berstein et al. |

(List continued on next page.)

FOREIGN PATENT DOCUMENTS

| | | |
|---|---|---|
| EP | 0189329 | 7/1986 |
| JP | 03-063041 | 3/1991 |
| WO | WO 90/01300 | 2/1990 |
| WO | WO 91/19529 | 12/1991 |
| WO | WO 94/05361 | 3/1994 |
| WO | WO 95/22284 | 8/1995 |
| WO | WO 95/24159 | 9/1995 |

OTHER PUBLICATIONS

Rosenschein et al., "Experimental ultrasonic angioplasty: disruption of atherosclerotic plaques and thrombi in vitro and arterial recanalization in vivo" (1990) *JACC* 15(3):711–717.

(List continued on next page.)

*Primary Examiner*—Mark Bockelman
(74) *Attorney, Agent, or Firm*—Townsend and Townsend and Crew LLP

(57) ABSTRACT

A catheter comprises a catheter body having an oscillating driver, an interface surface mechanically coupled to the driver, and an inflatable balloon disposed near the interface surface. The balloon may be an angioplasty balloon, in which case the interface surface will deliver ultrasonic or other vibratory energy into a blood vessel as part of an angioplasty or related procedure. Alternatively, the catheter may comprise a pair of axially spaced-apart isolation balloons, in which case the interface surface can deliver ultrasonic or other vibratory energy into a treatment region defined between said balloons. The energy can thus act to mix or enhance penetration of a treatment held between said balloons in performing a vascular treatment procedure.

6 Claims, 9 Drawing Sheets

U.S. PATENT DOCUMENTS

| | | |
|---|---|---|
| 5,181,920 A | 1/1993 | Mueller et al. |
| 5,197,946 A | 3/1993 | Tachibana |
| 5,267,954 A | 12/1993 | Shimada et al. |
| 5,267,985 A | 12/1993 | Shimada et al. |
| 5,269,291 A | 12/1993 | Carter |
| 5,269,297 A | 12/1993 | Weng et al. |
| 5,279,546 A | 1/1994 | Mische et al. |
| 5,282,785 A * | 2/1994 | Shapland et al. |
| 5,286,254 A | 2/1994 | Shapland et al. |
| 5,304,115 A | 4/1994 | Pflueger et al. |
| 5,315,998 A | 5/1994 | Tachibana et al. |
| 5,318,014 A | 6/1994 | Carter |
| 5,324,255 A | 6/1994 | Passafaro et al. |
| 5,342,292 A | 8/1994 | Nita |
| 5,344,395 A | 9/1994 | Whalen et al. |
| 5,362,309 A | 11/1994 | Carter |
| 5,380,273 A | 1/1995 | Dubrul et al. |
| 5,397,301 A | 3/1995 | Pflueger et al. |
| 5,447,509 A | 9/1995 | Mills et al. |
| 5,456,259 A | 10/1995 | Barlow et al. |
| 5,458,568 A | 10/1995 | Racchini et al. |
| 5,458,631 A | 10/1995 | Xavier |
| 5,462,523 A | 10/1995 | Samson et al. |
| 5,465,725 A | 11/1995 | Seyed-Bolorforosh |
| 5,474,530 A | 12/1995 | Passafaro et al. |
| 5,474,531 A | 12/1995 | Carter |
| 5,609,606 A | 3/1997 | O'Boyle |
| 5,611,807 A | 3/1997 | O'Boyle |
| 5,672,153 A | 9/1997 | Lax et al. |
| 5,713,848 A | 2/1998 | Dubrul et al. |
| 5,728,123 A | 3/1998 | Lemelson et al. |
| 5,846,218 A * | 12/1998 | Brisken et al. |
| 5,893,840 A * | 4/1999 | Hull et al. |
| 6,198,944 B1 * | 3/2001 | Hollenbach et al. |
| 6,287,272 B1 * | 9/2001 | Brisken et al. |

OTHER PUBLICATIONS

Tachibana, "Enhancement of fibrinolysis with ultrasound energy" (1992) *J. Vascular & Interventional Radiography* 3(2):299–303.

Yumita et al., "Synergistic effect of ultrasound and hematoporphyrin on sarcoma 180" (1990) *Japan J. Cancer Res.* 81:304–308.

* cited by examiner

BALLOON CATHETERS HAVING ULTRASONICALLY DRIVEN INTERFACE SURFACES AND METHODS FOR THEIR USE

CROSS-REFERENCES TO RELATED APPLICATIONS

The present application is a continuation of application Ser. No. 09/205,061, filed on Dec. 4, 1998, now U.S. Pat. No. 6,287,272 which was a continuation-in-part of application Ser. No. 08/708,589, filed on Sep. 5, 1996, now U.S. Pat. No. 5,846,218. The full disclosures of each of these applications is incorporated herein by reference.

BACKGROUND OF THE INVENTION

1. Field of the Invention

The present invention relates generally to medical devices and methods. More particularly, the present invention relates to apparatus and methods for performing angioplasty, stent delivery, and related procedures using balloon catheters having ultrasonically oscillated surfaces which can impart energy to a blood vessel being treated.

Despite the growing sophistication of medical technology, vascular (blood vessel) diseases, such as acute myocardial infarction (heart attack) and peripheral arterial thrombosis (blood clots in leg arteries), remain a frequent, costly, and very serious problem in health care. Current methods of treatment, often expensive, are not always effective. In the U.S. alone, the cost of treatment and support and the loss of productivity due to vascular diseases together exceed $40 billion per year.

The core of the problem is that diseased sites within the blood vessels narrow and eventually become completely blocked as a result of the deposition of fatty materials, cellular debris, calcium, and/or blood clots, thereby blocking the vital flow of blood. Current treatments include drugs, interventional devices, and/or bypass surgery. High doses of thrombolytics (clot-dissolving drugs) are frequently used in an effort to dissolve the blood clots. Even with such aggressive therapy, thrombolytics fail to restore blood flow in the affected vessel in about 30% of patients. In addition, these drugs can also dissolve beneficial clots or injure healthy tissue causing potentially fatal bleeding complications.

While a variety of interventional devices are available, including angioplasty, atherectomy, and laser ablation catheters, the use of such devices to remove obstructing deposits may leave behind a wound that heals by forming a scar. The scar itself may eventually become a serious obstruction in the blood vessel (a process known as restenosis). Also, diseased blood vessels being treated with interventional devices sometimes develop vasoconstriction (elastic recoil), a process by which spasms or abrupt reclosures of the vessel occur, thereby restricting the flow of blood and necessitating further intervention. Approximately 40% of treated patients require additional treatment for restenosis resulting from scar formation occurring over a relatively long period, typically 4 to 12 months, while approximately 1-in-20 patients require treatment for vasoconstriction, which typically occurs from 4 to 72 hours after the initial treatment.

The use of ultrasonic energy has been proposed both to mechanically disrupt clot and to enhance the intravascular delivery of drugs to dissolve clot and inhibit restenosis. Ultrasonic energy may be delivered intravascularly using specialized catheters having an ultrasonically vibrating surface at or near their distal ends.

It would be desirable to provide improved devices, systems, and methods, for treating vascular diseases, particularly stenotic diseases which occlude the coronary and other arteries. In particular, it would be desirable to provide methods and devices for enhancing the performance of angioplasty procedures, where the ability to introduce an angioplasty catheter through a wholly or partly obstructed blood vessel lumen can be improved. Moreover, it would be desirable to provide mechanisms as part of an angioplasty catheter, which mechanisms can assist in initial balloon deployment and/or decrease the likelihood of subsequent clot formation and restenosis. The devices, systems, and methods, should further be useful with other procedures which employ balloon catheters, including stent deployment and drug delivery, where drug delivery can be achieved by deploying a pair of spaced-apart balloons for defining a treatment region therebetween.

It would be desirable to provide improved devices, systems, and methods, for treating vascular diseases, particularly stenotic diseases which occlude the coronary and other arteries. In particular, it would be desirable to provide methods and devices for enhancing the performance of angioplasty procedures, where the ability to introduce an angioplasty catheter through a wholly or partly obstructed blood vessel lumen can be improved. Moreover, it would be desirable to provide mechanisms as part of an angioplasty catheter, which mechanisms can assist in initial balloon deployment and/or decrease the likelihood of subsequent clot formation and restenosis. The devices, systems, and methods, should further be useful with other procedures which employ balloon catheters, including stent deployment and drug delivery, where drug delivery can be achieved by deploying a pair of spaced-apart balloons for defining a treatment region therebetween.

2. Description of the Background Art

A catheter system having a pair of spaced-apart balloons with a coiled piezoelectric strip therebetween is described in U.S. Pat. No. 5,279,546. Catheters having elongate ultrasonic transmission elements and inflatable cuffs are described in U.S. Pat. Nos. 5,397,301; 5,304,115; and 4,870,953. A tunneling catheter having a radiofrequency, laser, or ultrasonic active distal end disposed within an angioplasty catheter is described in EP 189 329. An atherectomy catheter having an ultrasonically enhanced blade disposed adjacent an asymmetrically mounted balloon is described in U.S. Pat. No. 5,085,662. Phonophoresis transducers disposed within porous, inflatable balloons are suggested in U.S. Pat. Nos. 5,286,254 and 5,282,785. Other catheters having ultrasonic elements with the capability of delivering thrombolytic and other liquid agents are described in U.S. Pat. Nos. 5,362,309; 5,318,014; 5,315,998; 5,197,946; 5,380,273; 5,344,395; 5,342,292; 5,324,255; 5,269,297; 5,267,954; 4,808,153; 4,692,139; and 3,565,062; in WO 90/01300; and in Tachibana (1992) JVIR 3:299–303. A rigid ultrasonic probe intended for treating vascular plaque and having fluid delivery means is described in U.S. Pat. No. 3,433,226. An ultrasonic transmission wire intended for intravascular treatment is described in U.S. Pat. No. 5,163,421 and Rosenschein et al. (1990) JACC 15:711–717. Ultrasonic enhancement of systemic and localized drug delivery is described in U.S. Pat. Nos. 5,267,985; and 4,948,587; in WO 94/05361 and WO 91/19529; in JP 3-63041; and Yumita et al. (1990) Jpn. J. Cancer Res. 81:304–308. An electrosurgical angioplasty catheter having ultrasound enhancement is described in U.S. Pat. No. 4,936,281. An infusion and drainage catheter having an ultrasonic cleaning mechanism is described in U.S. Pat. No. 4,698,058. Angioplasty balloon catheters having axial blade atherectomy, ultrasonic imaging, and rotary blade atherectomy devices at their distal ends are described in U.S. Pat. Nos. 5,053,044; 5,117,831; and 5,181,920, respectively.

This application is related to the following commonly assigned patents and applications: U.S. Pat. Nos. 5,725,494; 5,728,062; 5,735,811; 5,931,805; U.S. Pat. Nos. 09/033,834; 09/223,230; 09/635,033; and 09/653,678. The full disclosures of each of these patents and pending applications are incorporated herein by reference.

BRIEF SUMMARY OF THE INVENTION

According to the present invention, improved devices and systems are provided which combine both an inflatable balloon and an axially oscillated interface surface on a single catheter device. The devices and systems are useful for a number of intervascular procedures, including (1) angioplasty and related procedures, such as stent deployment, where ultrasonic energy delivered by the interface surface can soften the stenotic material in the blood vessel to facilitate deployment and initial treatment and can also reduce residual clot in the treated region in order to lessen the likelihood of restenosis, and (2) drug delivery methods where balloons are used to isolate a treatment region and at least one of the balloons is coupled to the interface surface so that oscillation of the balloon(s) enhances mixing and penetration of a treatment medium localized between the balloons.

The catheters of the present invention will comprise a catheter body having a proximal end and a distal end. An oscillating driver is disposed at or near the distal end of the catheter body, and an interface surface is mechanically coupled to the driver so that the surface can be axially oscillated relative to the catheter body. An inflatable balloon is also disposed on the catheter body near the interface surface, where the balloon can be used for angioplasty, stent deployment, or the like, and optionally can be combined with a second balloon to define a drug treatment region therebetween.

In a first specific embodiment, the interface surface comprises a distal tip which extends laterally over the distal end of the catheter body. An angioplasty or stent delivery balloon is disposed on the catheter body proximal to the interface surface. Optionally, the interface surface can further include a cylindrical portion which extends over an axial surface of the catheter body. In either case, a distal end of the balloon can be secured directly to the interface surface so that the balloon itself is caused to directly oscillate as the interface surface is oscillated by the driver.

In use, the catheters having interface surfaces including a laterally disposed distal tip will facilitate penetration of the catheter through a partly or wholly occluded stenotic region within a blood vessel. The distal tip will be driven, and the catheter advanced through the stenotic material, with the ultrasonic energy softening the stenotic material to facilitate advance of the catheter. The balloon, which is proximal to the distal tip, may then be used for either an angioplasty procedure, stent delivery, or both. In either case, the interface surface on the catheter can thereafter be used to further treat the stenotic region with ultrasonic energy to reduce the amount of clot remaining in order to lessen the likelihood of further clot formation and restenosis.

In a second specific embodiment, the interface surface is disposed at least partly within the inflatable balloon on the catheter body. Preferably, the interface surface and associated oscillatory driver are both located entirely within the inflatable balloon, so that the interface surface can be used to transfer ultrasonic energy directly into the inflation medium used to inflate the balloon. Alternatively, the balloon is mounted so that at least one of its forward end and/or distal end is secured to a cylindrical interface surface. In this way, after balloon inflation, the interface surface will directly oscillate one or both ends of the balloon. The catheters of this type will be particularly useful for performing enhanced angioplasty procedures, optionally with stent delivery.

A third exemplary embodiment of the catheter of the present invention comprises a pair of spaced-apart inflatable balloons on the catheter body. A cylindrical interface surface is disposed between the balloons, with at least one of the distal end of the proximal-most balloon and the proximal end of the distal-most balloon being secured to the interface member. A fluid delivery lumen is provided within the catheter so that a treatment medium can be delivered to the region between the balloons when the balloons are expanded in a blood vessel. Mixing and/or penetration of the treatment medium is enhanced by ultrasonic oscillation of the cylindrical interface surface when the treatment medium is present.

DESCRIPTION OF THE SPECIFIC EMBODIMENTS

Figure 1:
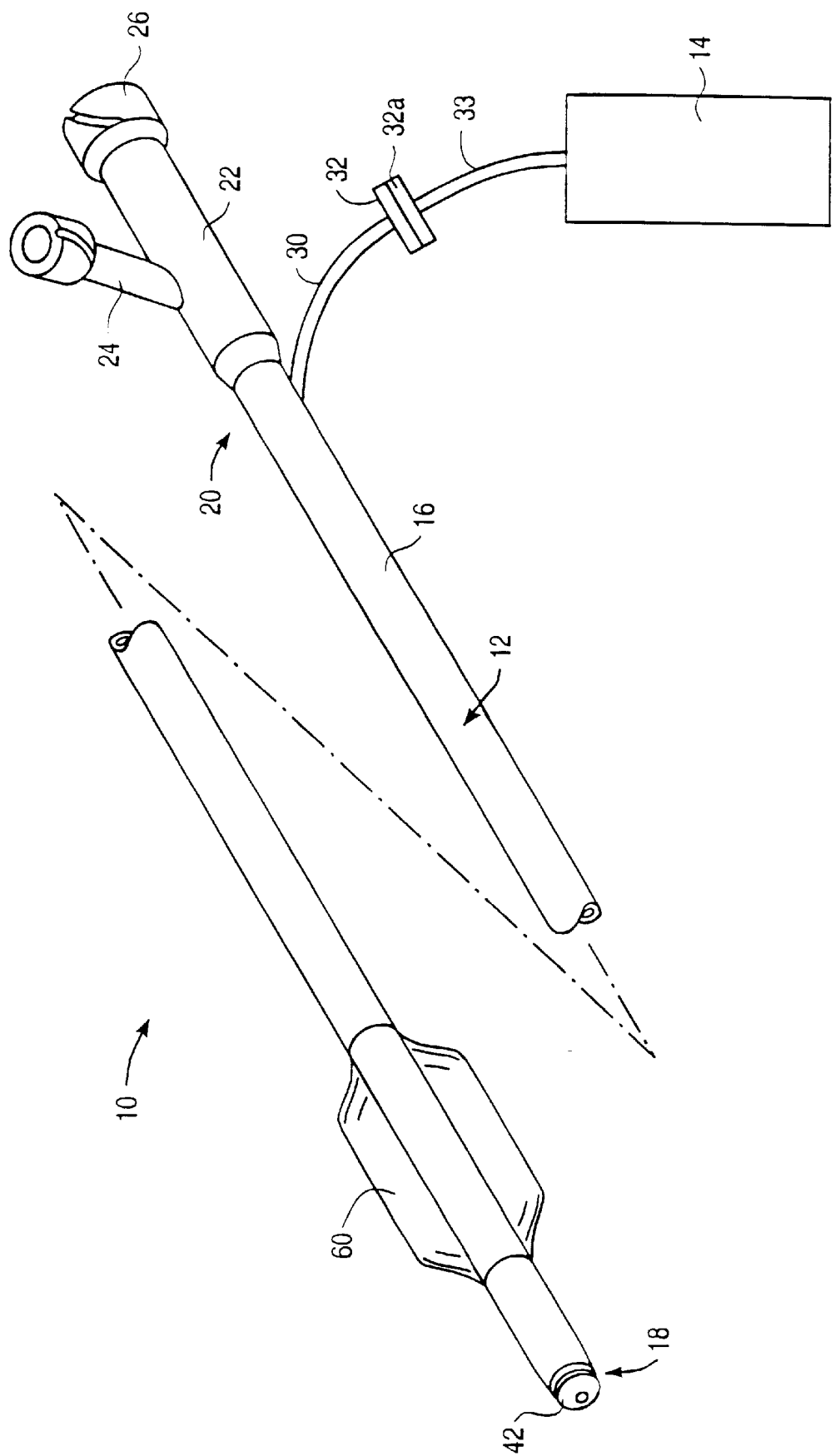
FIG. 1 illustrates an exemplary catheter incorporating an interface surface having a distal tip and an angioplasty balloon disposed proximally of the interface surface, constructed in accordance with the principles of the present invention.

The present invention provides apparatus and methods for the treatment of luminal conditions, particularly for the treatment of diseases of the coronary and peripheral vasculature. Specific conditions include coronary and peripheral arterial disease and thrombosis. The apparatus and methods are useful for primary treatment of such diseases, where the purpose is to ablate, dissolve, or otherwise disrupt the clot, plaque, or other stenotic lesions which are responsible for the disease. For example, catheters constructed according to the principles of the present invention can be used to directly engage and transmit vibratory, usually ultrasonic, energy into the stenotic material in order to mechanically disrupt the material to open the associated blood vessel lumen. The catheters of the present invention will also include at least one inflatable balloon in order to perform procedures which combine use of the balloon with the ability to deliver ultrasonic or other vibratory energy.

Usually, the balloons will be angioplasty balloons useful for engaging and dilatating stenotic regions within a blood vessel. In such cases, the vibratory energy may be used either to enhance initial penetration of the catheter so that the angioplasty balloon can be positioned within the stenotic region (e.g. by softening or disrupting the stenotic material prior to balloon positioning), to soften the stenotic material while the balloon is being expanded with or without a stent, and/or to treat the stenotic region within the blood vessel after the balloon has been used to perform angioplasty, stent placement, or the like. In the latter case, the transfer of ultrasonic energy can reduce the presence of residual clot which can serve as nuclei for subsequent clot formation and restenosis.

The catheters may also include a pair of spaced-apart balloons, where the balloons define a treatment region therebetween which is useful to enhance the administration of therapeutic agents, where the therapeutic agents are primarily responsible for the disruption of the stenotic material and/or lessening of restenosis subsequent to angioplasty. In such cases, the vibratory energy will be relied on to agitate and promote the penetration of the therapeutic agent into the stenotic material. Suitable therapeutic agents include known thrombolytic and fibrinolytic drugs, such as heparin, tissue plasminogen activator (tPA), urokinase, streptokinase, and the like.

The catheters of the present invention will comprise a catheter body having a proximal end and distal end. The catheter body will have dimensions and physical characteristics selected for the particular use. For vascular applications, the length of the catheter body will typically be from 50 cm to 200 cm, usually being from 75 cm to 150 cm, and the diameter will be from 1 mm to 5 mm, usually being from 2 mm to 4 mm. The diameter of the catheter body may vary over its length, and different portions of the length may be formed from different materials. In the exemplary embodiment, the catheter body will comprise a single extrusion having at least one lumen therethrough for providing an inflation medium to the balloon. That or another lumen, will usually be capable of receiving a guidewire, and may also be capable of delivering therapeutic agents and/or carrying electrical wires for connection from the proximal end of the catheter body to the distal end. Alternatively, the catheter body may include separate lumens for balloon inflation, delivering therapeutic agent(s), routing electrical wires for connection to the ultrasonic transducer, or other purposes.

The catheter body may be reinforced over all or a portion of its length. Conventional reinforcement materials include wire braids, wire meshes, wire coils, helical ribbons, and the like.

When employed with a guidewire for placement within the vasculature, the catheter body may have an "over-the-wire" design or a "rapid exchange" design. In the former case, the guidewire lumen will extend substantially through the entire length of the catheter body. In the latter case, the guidewire lumen will terminate in a proximal guidewire port located relatively near the distal end of the catheter body, usually within 50 cm, more usually within 30 cm, and often within 25 cm or less. Usually, a proximal housing will be secured to the proximal end of the catheter body, where the housing includes a guidewire port, a therapeutic agent infusion port, an electrical connector, and the like.

A longitudinally vibrating assembly is secured at or near the distal end of the catheter body. The assembly will include at least one interface surface, usually present on an interface member, which is vibrated at a desired frequency, wherein the interface surface is oriented to transmit vibrations to the fluid environment surrounding the distal end of the catheter. The vibrating assembly will usually be attached directly to the distal end of the catheter body but also could be disposed partially or totally within the distal end of the catheter body. Usually, the vibrating assembly will have a relatively short length, typically being below 2 cm, preferably being below 1 cm, and typically being in the range from about 0.4 cm to 1.5 cm, more usually in the range from about 0.6 cm to 1 cm. The assembly will preferably have a low profile (narrow diameter) to facilitate vascular or other intraluminal introductions, typically having a diameter below 6 mm, usually in the range from 1 mm to 5 mm, more usually in the range from 2 mm to 4 mm.

In a first exemplary embodiment of the present invention, the interface surface will be forwardly disposed so that the surface may engage intraluminal obstructions as the catheter is advanced through the body lumen, such as a blood vessel. In a second exemplary embodiment, the interface member may also or alternatively include an interface surface where at least a portion of the surface is disposed circumferentially about the catheter body. The circumferential portion will usually be a cylinder, and the interface member and surface will oscillate axially (i.e., back and forth generally in the direction of the catheter body). The energy will radiate away from the cylindrical surface of the interface member in a generally uniform pattern, i.e., isotropically (radially outward). Such uniform radiation is particularly advantageous for softening stenotic material and/or for enhancing the penetration of therapeutic agents into a length of an intraluminal wall adjacent a cylindrical interface surface.

In the exemplary embodiments, the cylindrical interface surface will typically have a length in the range from 4 mm to 30 mm, preferably from 6 mm to 15 mm. The outer diameter of the cylindrical surface will typically be in the range from 2 mm to 5 mm, more usually from 3 mm to 4 mm. The interface member may further include a forwardly disposed lateral surface, typically being formed laterally at the distal end of the cylindrical surface. The lateral surface may itself be flat, convex (in the form of a forwardly disposed dome at the distal end of the cylindrical surface), concave, or irregular. The cylindrical surface and/or the forwardly disposed lateral surface may also have surface irregularities formed therein. For example, a plurality of ridges, protrusions, or the like, may be provided for enhancing the transfer of oscillatory motion into the fluid adjacent the surface.

An oscillating driver will be provided on the catheter body for oscillating the interface member in a desired manner. Usually, the driver will be separate from the interface member. In some cases, however, it may be possible to provide an oscillatory driver which also defines the interface surface, particularly for radially oscillating drivers as described in copending applications Ser. Nos. 08/565,575; 08/566,739; and 08/566,740, the full disclosures of which have previously been incorporated herein by reference. The drivers will usually be ultrasonic transducers, including tubular piezoelectric transducers, piezoelectric stack transducers, magnetostrictive drivers, dectostrictive drivers, or the like. Optionally, the drivers may be incorporated in a resonant drive assembly, typically including a spring element attaching the interface member to the catheter body, where the ultrasonic driver is a longitudinally oscillating driver disposed between the catheter body and the interface member. Longitudinally oscillating drivers will usually be selected to oscillate with an amplitude in the range from 0.05 $\mu$m to 50 $\mu$m, often from 0.1 $\mu$m to 20 $\mu$m, preferably from 0.5 $\mu$m to 4 $\mu$m. The details of such drivers and resonant drive assemblies are set forth in copending application Ser. No. 08/565,575, assigned to the assignee of the present application, the full disclosure of which is incorporated herein by reference.

The catheters of the present invention will further comprise expansible balloon members disposed proximally and/or distally of the interface surface(s) of the interface member. The expansible members, typically in the form of inflatable non-compliant and/or elastomeric balloons, may be utilized to perform angioplasty or engage a luminal wall to isolate a luminal region to be treated. Materials and designs for incorporating balloons in intravascular and other catheters are well known in the art.

Referring now to FIG. 1, a catheter system 10 comprising a catheter 12 constructed in accordance with the principles of the present invention and a power supply 14 is illustrated. The catheter 12 includes a catheter body 16 having a distal end 18 and a proximal end 20, and a proximal housing 22 having a balloon inflation port 24 and a guidewire port 26. Usually, the catheter 12 will have at least a second lumen (not illustrated) for accommodating wires transmitting energy from the power supply 14 to an ultrasonic transducer, as described hereinafter. Cable 30 extends from the proximal end 20 of the catheter body 16 and includes a connector 32 which mates with connector 32a on cable 33 from the power supply 14. The power supply 14 will be selected to provide an appropriate current source for driving an ultrasonic transducer, as described in more detail herein below.

The power supply and transducer will be selected so that the ultrasonic driver typically operates in the range from 1 kHz to 300 kHz, preferably from 20 kHz to 80 kHz. For example, the power supply 14 may comprise a conventional signal generator, such as those commercially available from suppliers such as Hewlett-Packard, Palo Alto, Calif., and Tektronics, Portland, Oreg., and a power amplifier, such as those commercially available from suppliers such as ENI, Rochester, N.Y., and Krohn-Hite Corporation, Avon, Mass.

Figure 2:
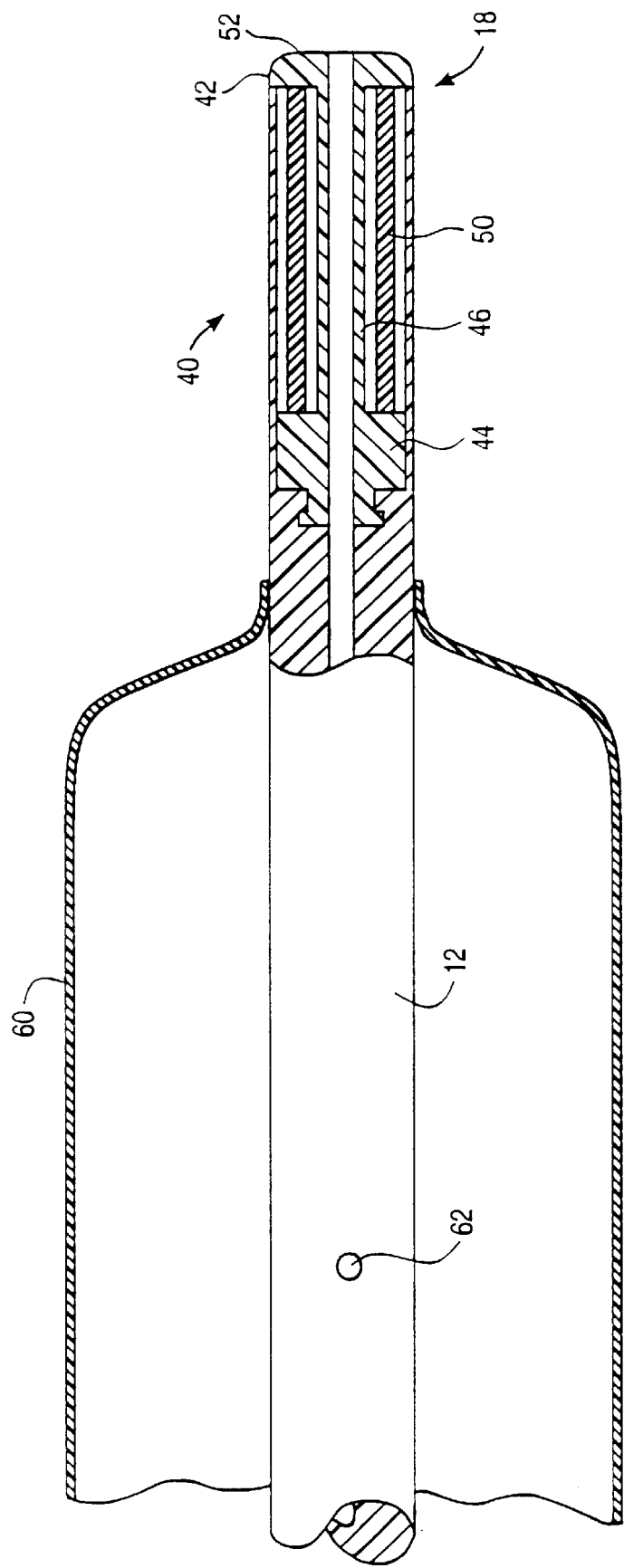
FIG. 2 is a detailed view of the distal end of the catheter of FIG. 1, shown in partial section.

Referring now to FIGS. 1 and 2, the catheter 12 includes a vibratory assembly 40 at its distal end 18. The vibratory assembly 40 includes a distal tip 42 connected to a tail mass 44 by a spring member 46. Conveniently, the distal tip 42, tail mass 44, and connecting spring 46 may be integrally formed, although such integral construction is not a requirement for the present invention. An oscillatory drive assembly 50 is disposed between a proximal surface of the distal tip 42 and a distal surface of the tail mass 44, and may comprise a cylindrical piezoelectric element, such as those described in copending application Ser. Nos. 08/565,575 and 08/566,739, the full disclosures of which have been incorporated herein by reference. Other longitudinal drivers, such as stacked piezoelectric disks and magnetostrictive drivers (as described in copending application Ser. No. 08/566,740, the full disclosure of which has previously been incorporated herein by reference), may also find use. The vibratory assembly 40 will be able to longitudinally oscillate the distal tip 42 so that a forwardly disposed lateral surface 52 may be longitudinally oscillated, typically with an amplitude in the range from 0.05 $\mu$m to 20 $\mu$m.

An angioplasty balloon 60 is disposed on the catheter body 12 proximal to the distal tip 42, typically being spaced-apart from the tip by a length in the range from 0 mm to 30 mm, typically from 2 mm to 10 mm. The balloon 60 may be inflated through an inflation port 62 which is connected to inflation port 24 on the proximal housing 22.

Figure 3:
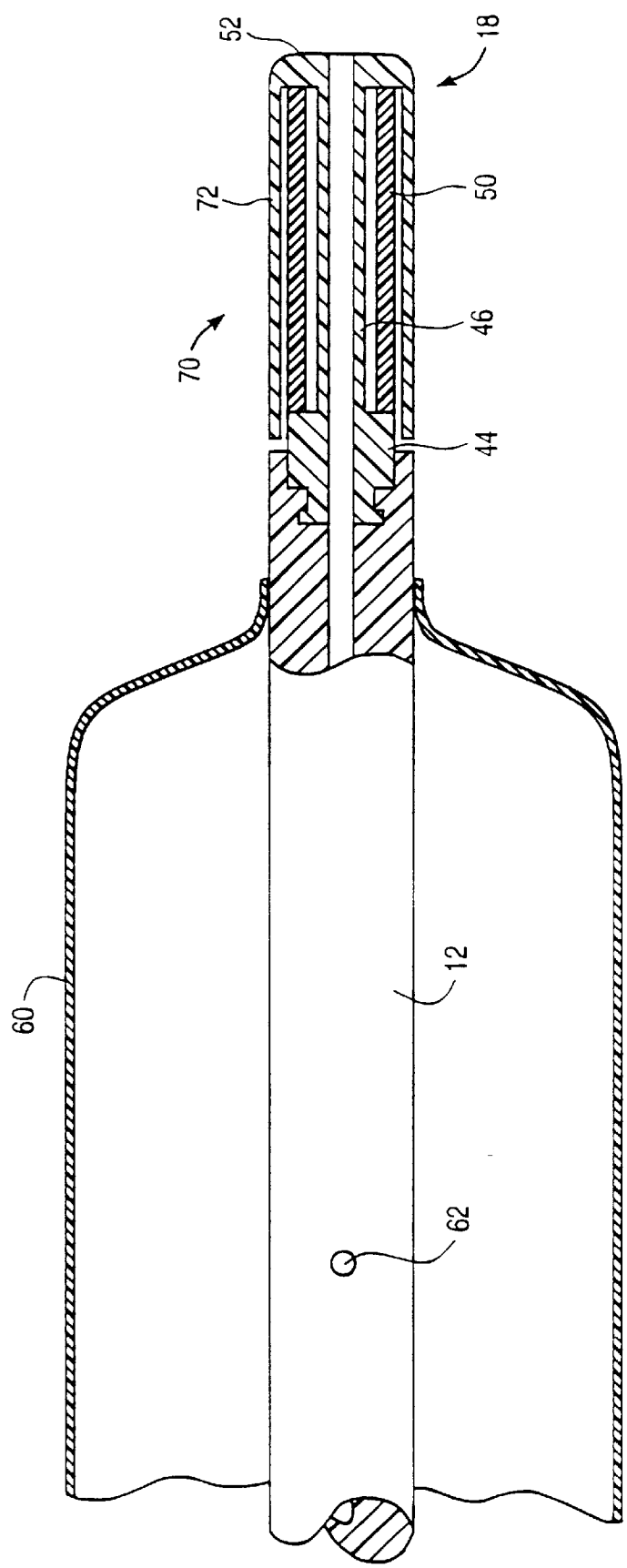
FIG. 3 is a detailed view of the distal end of a first alternative embodiment of the catheter of FIG. 1, wherein the interface surface further extends over a cylindrical portion of the catheter body, shown in partial section.

The distal end of an alternative embodiment of the catheter of FIG. 1 is illustrated in FIG. 3. There, a vibratory assembly 70 at the distal end 18 (all common elements of the alternative embodiment will be given the same reference numbers) of the catheter body 12. The vibratory assembly 70 includes a tail mass 44, and a spring 46, each of which are identical to the same elements in the catheter of FIGS. 1 and 2. Instead of the distal tip 42, the catheter of FIG. 3 includes an interface surface comprising a cylindrical interface surface which extends over a length of the catheter body from 4 mm to 30 mm, preferably from 6 mm to 15 mm. The distal end of the interface surface terminates in a lateral surface 52 which may have generally the same geometry as that of the catheter of FIGS. 1 and 2. The oscillatory driver 50 will generally be the same as that described previously.

The primary difference between the vibratory assembly 40 and vibratory assembly 70 is in the nature of the interface surface. The interface surface defined by distal tip 42 and FIGS. 1 and 2 provides only a forwardly disposed, lateral interface 52 surface which is useful for engaging stenotic material directly in front of the catheter. While the vibratory assembly 70 includes an equivalent forwardly disposed interface surface, it further includes a circumferentially disposed cylindrical surface which can impart vibratory energy radially outwardly into fluid surrounding the catheter tip. The nature and advantages of such cylindrical and other laterally disposed interface surfaces are described in more detail in copending application Ser. No. 08/566,739, the full disclosure of which has previously been incorporated herein by reference.

Figure 4:
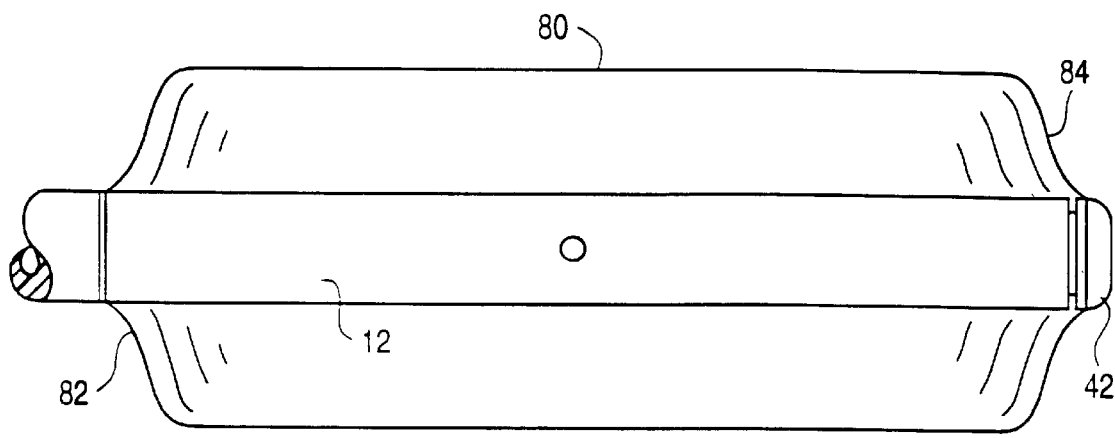
FIG. 4 is a detailed view of the distal end of a second alternative embodiment of the catheter of FIG. 1, wherein the angioplasty balloon is attached at its distal end to the interface surface.
Figure 5:
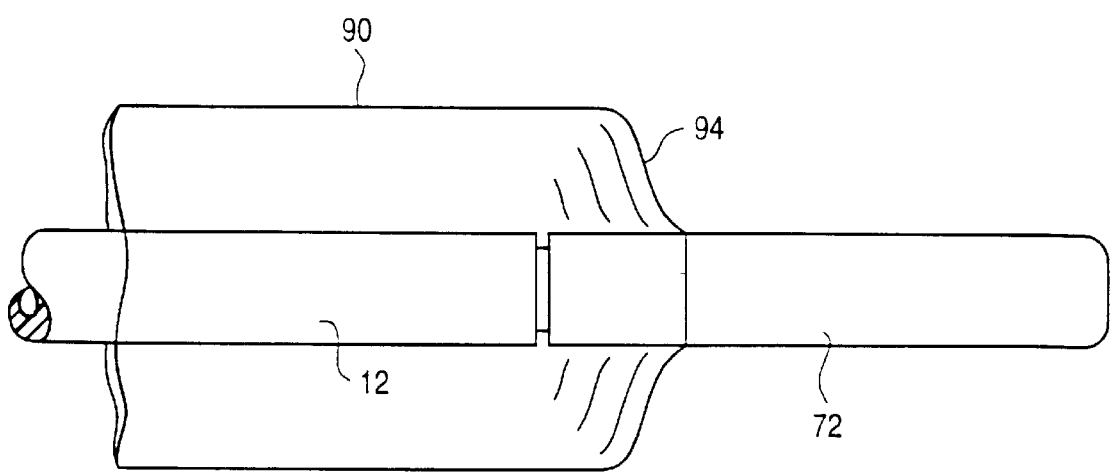
FIG. 5 is a detailed view of the distal end of a third alternative embodiment of the catheter of FIG. 1, wherein the distal end of the angioplasty balloon is attached to the cylindrical portion of the interface surface of the first alternative embodiment of FIG. 2.

The catheters of FIGS. 1–3 each attach the angioplasty balloon directly to the catheter body. Thus, vibration of the interface surfaces of those catheters is not directly coupled to the balloon itself. Referring now to FIGS. 4 and 5, angioplasty balloons may be partly or wholly connected to the interface surfaces which are vibrated by the oscillatory drivers. For example, as illustrated in FIG. 4, a balloon 80 may be attached at its proximal end 82 to the catheter body 12 and at its distal end 84 to the distal tip 42. In this way, the distal end of the balloon 80 may be directly vibrated by the distal tip 42 in order to impart oscillatory energy to the balloon. The balloon may thus be directly vibrated and enhance the transfer of oscillatory energy into the fluid medium surrounding the catheter. Similarly, a balloon 90 may have its distal end 94 attached to the cylindrical interface surface 72 of the catheter of FIG. 3, as illustrated in FIG. 5.

Figure 6:
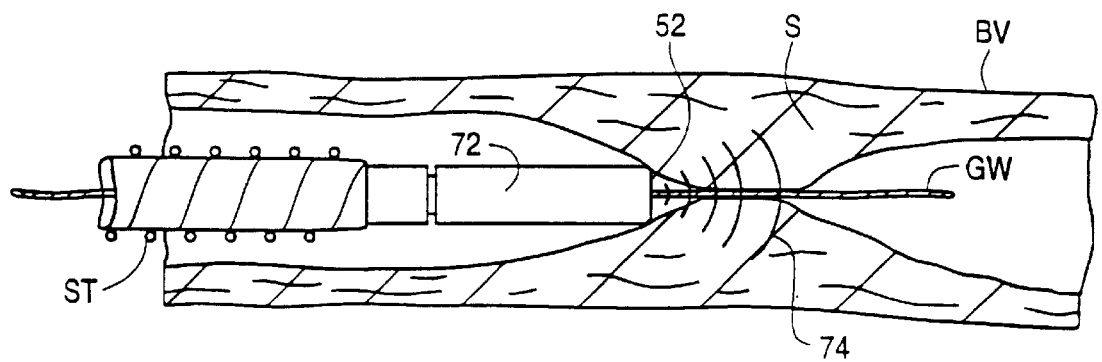
FIGS. 6–8 illustrate use of the catheter of FIG. 2 for penetrating a stenotic region within a blood vessel and expanding a vascular stent therein.
Figure 7:
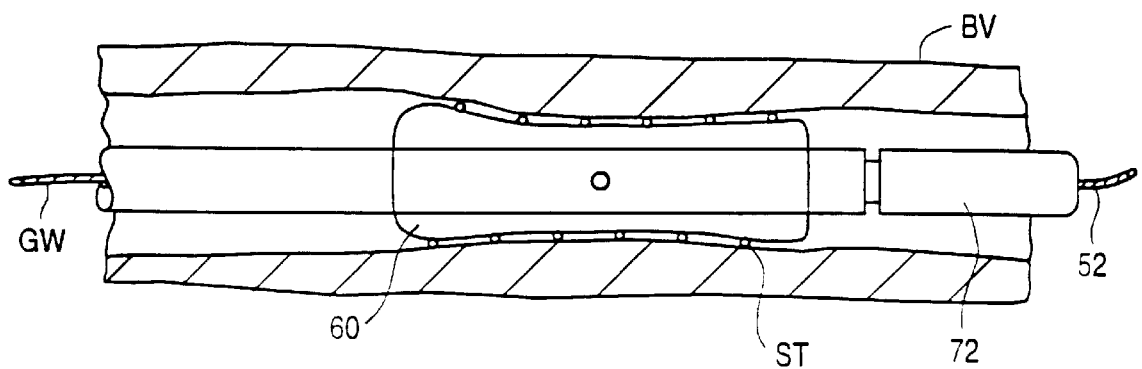
Figure 8:
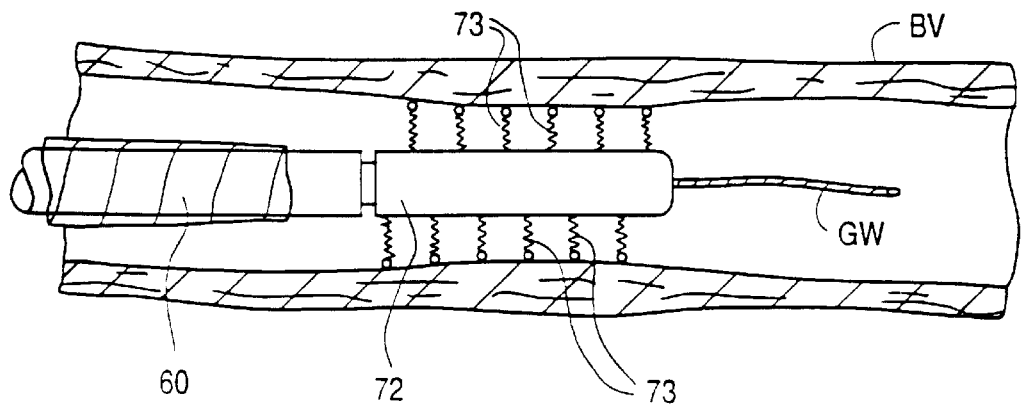

Referring now to FIGS. 6–8, the catheter of FIG. 3 may be used to perform angioplasty and optionally deliver a stent ST. Initially, the catheter is delivered over a guidewire GW until the distal interface surface 52 of the catheter engages the stenotic material S within a blood vessel BV. The oscillatory driver of the catheter is then actuated so that the distal surface 52 is longitudinally oscillated in order to soften the stenotic material S and enhance penetration of the catheter through the stenotic material. In particular, ultrasonic energy may be radiated forwardly in a pattern indicated by wave front lines 74, as shown in FIG. 6.

After the catheter has penetrated the material in the stenotic region S, the balloon 60 may be inflated, optionally expanding the stent ST, as illustrated in FIG. 7. After the region has been dilatated, and optionally the stent ST delivered, the catheter may be moved rearwardly so that the cylindrical surface 72 is aligned with the region that has been treated, as illustrated in FIG. 8. The catheter may again be actuated, and the cylindrical surface 72 will transfer ultrasonic wave energy into the medium surrounding the distal end of the catheter, as illustrated by the laterally extending transverse wave lines 73 from the surface. The ultrasonic energy will further reduce any residual clot or other stenotic materials which may be present after the dilatation in order to reduce the likelihood of restenosis.

Figure 9:
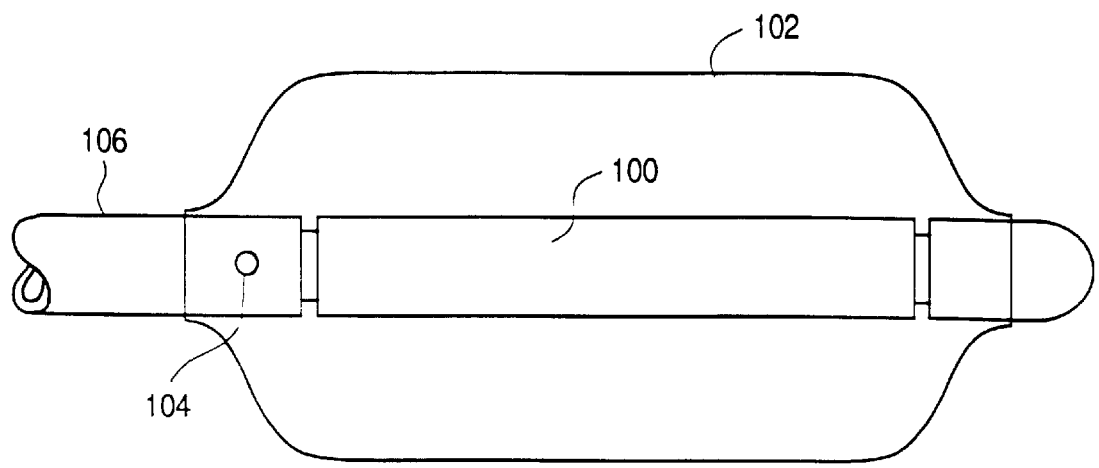
FIG. 9 illustrates the distal end of a fourth alternative embodiment of the catheter of the present invention, wherein a cylindrical interface surface is disposed entirely within an angioplasty balloon.
Figure 10:
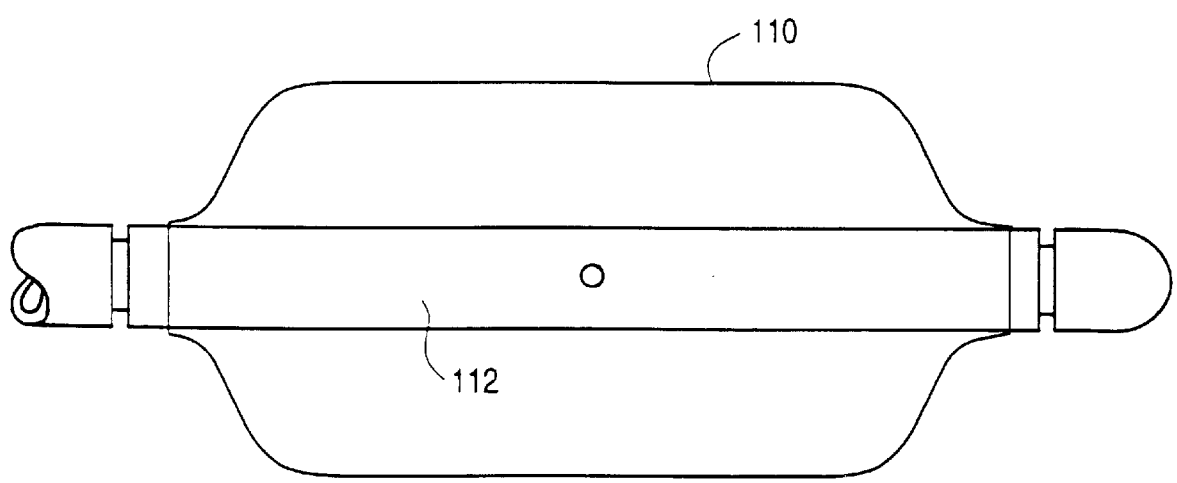
FIG. 10 illustrates a fifth alternative embodiment of the catheter of the present invention, wherein the angioplasty balloon is attached at both its proximal and distal ends to a cylindrical interface surface.
Figure 11:
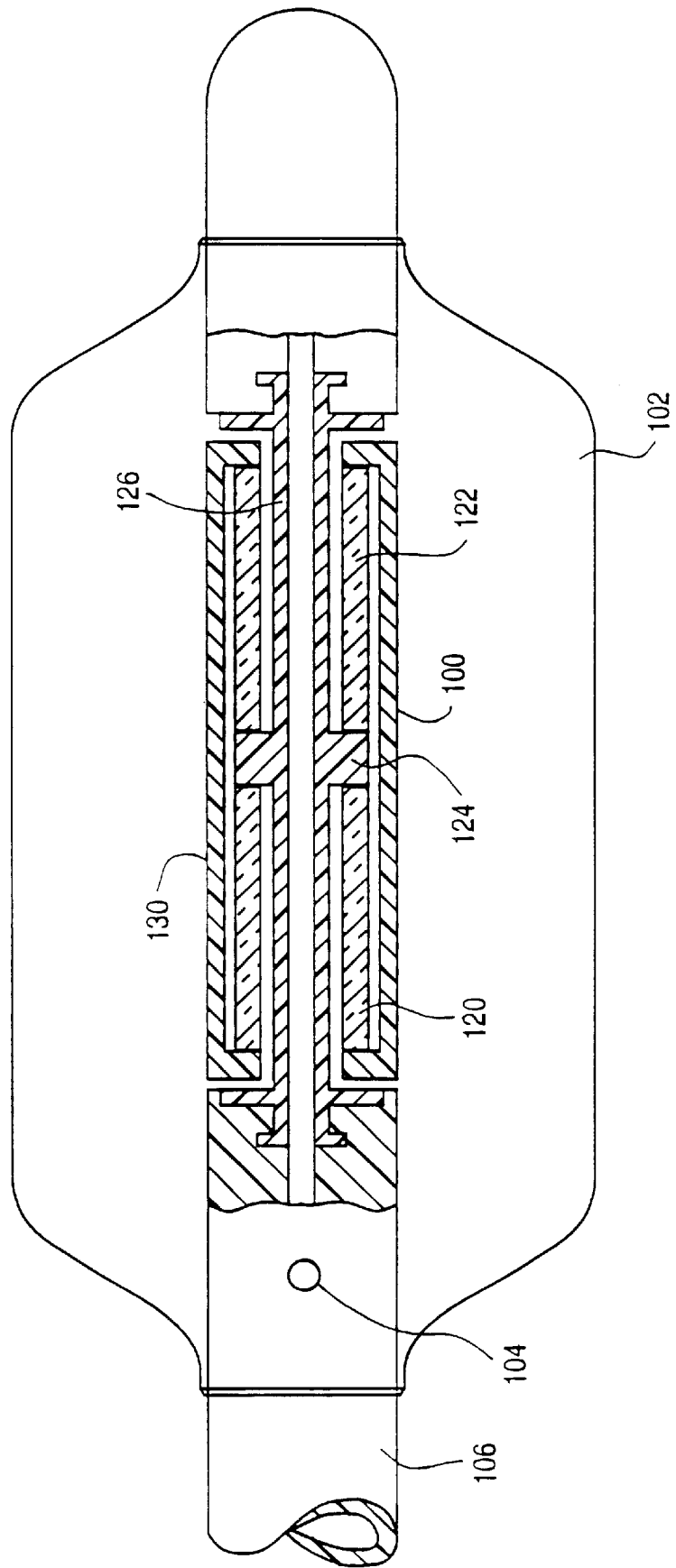
FIG. 11 is a view of the distal end of the catheter of FIG. 9, shown in partial section.

Referring now to FIGS. 9–11, further alternative embodiments of the catheter of the present invention will be illustrated. In FIG. 9, a cylindrical interface surface 100 is disposed completely within inflatable angioplasty balloon 102. An inflation port 104 is provided on the catheter body 106, and actuation of the oscillatory driver, as illustrated in FIG. 11, will impart transverse waves into the inflation medium within the balloon 102. In FIG. 10, a balloon 110 is attached at both its distal and proximal ends to a cylindrical interface surface 112. In this way, when the interface surface 112 is actuated, both ends of the balloon 112 will be longitudinally oscillated together with the surface.

Referring now to FIG. 11, a first tubular transducer 120 and a second tubular transducer 122 are disposed on the proximal and distal sides of a flange 124 which is located in the middle of a tubular holder 126. As illustrated, the transducers 120 and 122 are tubular piezoelectric transducers, but they could also be piezoelectric stack transducers, magnetostrictive drivers, or the like, as described in more detail in copending application Ser. Nos. 08/565,575; 08/566,739; and 08/566,740, the full disclosures of which have previously been incorporated herein by reference. In all cases, the transducers 120 and 122 will be wired so that they oscillate longitudinally in the same direction, but 180 out of phase. In this way, the total distance between the proximal end of transducer 120 and the distal end of transducer 122 will remain constant, while the ends of each transducer are displaced axially in a synchronous manner. An interface member 130 having the cylindrical interface surface 100 is attached to the respective ends of the first transducer 120 and the second transducer 122. In this way, the transducers will be driven in a longitudinally oscillating manner at a frequency determined by the characteristics of the transducers and the mass of the interface surface.

Figure 12:
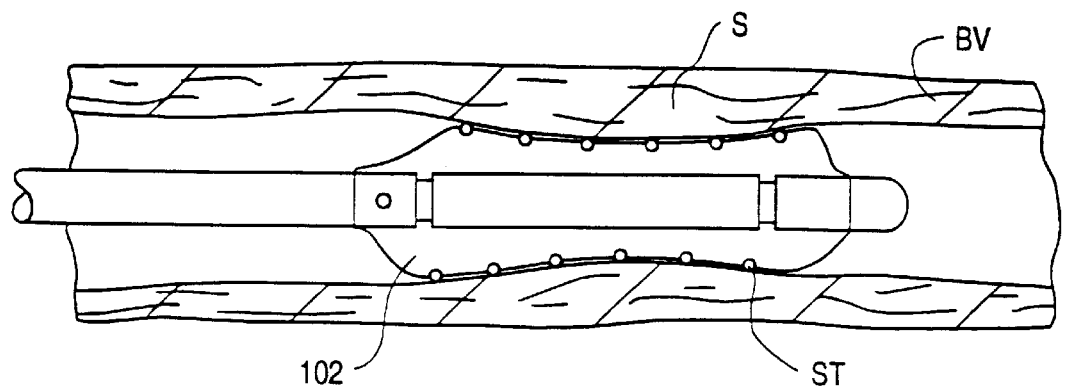
FIGS. 12 and 13 illustrate use of the catheter of FIG. 9 for expanding a stent within a stenotic region in a blood vessel.
Figure 13:
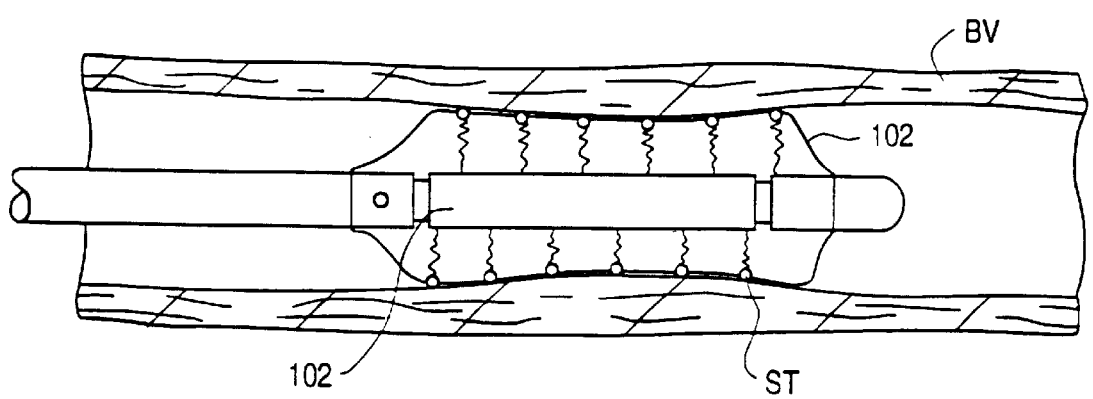

Referring now to FIGS. 12 and 13, the catheter of FIGS. 9 and 11 may be used to dilatate and optionally deliver a stent to a region of vascular stenosis S in a blood vessel BV. Initially, the balloon 102 carrying the stent ST is positioned within the region of stenosis S, and thereafter the balloon is inflated, as illustrated in FIG. 12. In order to further inflate the balloon and implant the stent ST, the transducers 120 and 122 are activated in order to longitudinally oscillate the cylindrical surface 102. Such oscillation induces transverse waves within the inflation medium within the balloon 102 as illustrated in FIG. 13. The energy will be farther transferred into the blood vessel wall, softening the stenotic material and enhancing expansion of the balloon 102 and stent ST.

Figure 14:
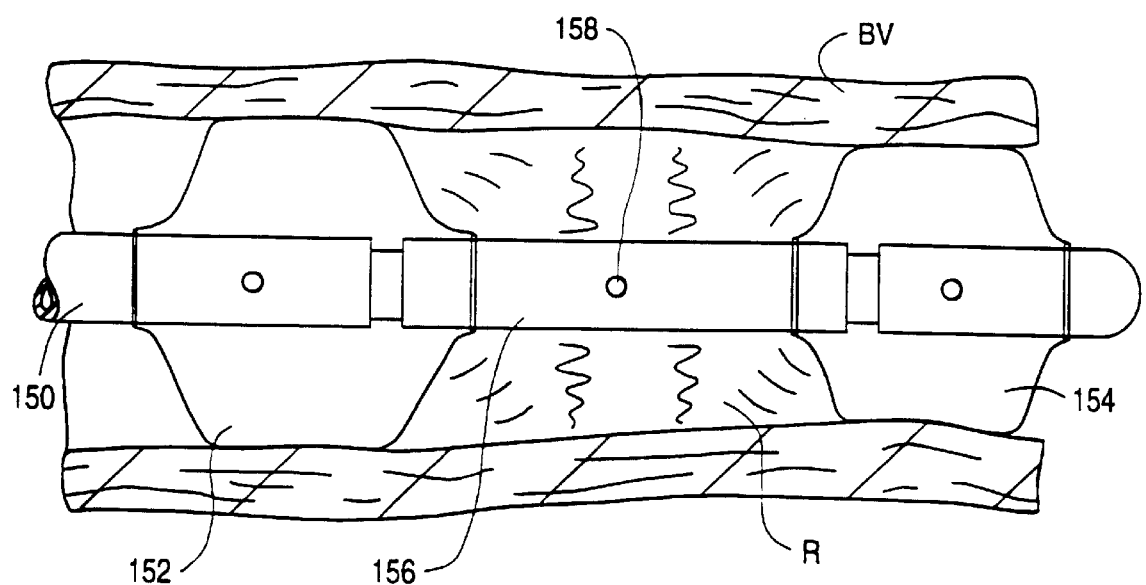
FIG. 14 illustrates a sixth alternative embodiment of the catheter of the present invention, wherein the catheter includes a pair of axially spaced-apart balloons and wherein the distal end of the proximal-most balloon and the proximal end of the distal-most balloon are each attached to a cylindrical interface surface disposed therebetween.

Referring now to FIG. 14, a catheter 150 having a proximal balloon 152 and a distal balloon 154 is illustrated. The balloons are axially spaced-apart, and a cylindrical interface surface 156 is disposed therebetween. The interface surface 156 may be constructed identically to the transducer assembly of FIG. 11, except that a fluid transfer port 158 will be provided in order to deliver a treatment medium to the volume between the spaced-apart balloons 152 and 154. In use, the spaced-apart balloons 152 and 154 will be inflated within a blood vessel BV to define a treatment region R therebetween. A liquid treatment medium is then introduced into the treatment region R through the delivery port 158. After the treatment medium is delivered to the treatment region, the cylindrical interface surface will be longitudinally oscillated in order to transfer transverse waves into the medium. The distal end of the proximal balloon 152 and proximal end of the distal balloon 154 are secured to opposite ends of the cylindrical interface surface 156. In this way, the inwardly disposed surfaces of each balloon are oscillated together with the interface surface 156. Thus, the balloons themselves can further act to impart vibratory energy into the treatment medium contained within the treatment region R.

Although the foregoing invention has been described in some detail by way of illustration and example, for purposes of clarity of understanding, it will be obvious that certain changes and modifications may be practiced within the scope of the appended claims.

What is claimed is:

1. A method for delivering a stent to a blood vessel, said method comprising:

positioning a catheter carrying a stent within the blood vessel;

inflating a balloon on the catheter to implant the stent; and activating a transducer on the catheter to deliver oscillatory waves into the blood vessel wall in the region of the stent, wherein a distal portion of the catheter oscillates longitudinally relative to a proximal portion.

2. A method as in claim 1, wherein the transducer is disposed within the balloon on the balloon catheter.

3. A method as in claim 2, wherein activating the transducer comprises transversely oscillating the transducer.

4. A catheter comprising:

a catheter body having a proximal and a distal end;

an interface surface within the balloon wherein the interface surface oscillates longitudinally along the catheter body relative to a proximal portion;

a transducer coupled to vibrate the interface surface;

an inflatable balloon on the catheter body, proximate the interface surface; and a stent carried over the balloon.

5. A catheter as in claim 4, wherein the balloon is over the interface surface.

6. A catheter as in claim 5, wherein the transducer is coupled to longitudinally oscillate the interface surface.

* * * * *